(12) United States Patent
Nishida et al.

(10) Patent No.: US 7,854,854 B2
(45) Date of Patent: Dec. 21, 2010

(54) QUATERNARY AMMONIUM SALT, ELECTROLYTE, ELECTROLYTE SOLUTION AND ELECTROCHEMICAL DEVICE

(75) Inventors: Tetsuo Nishida, Izumiotsu (JP);
Kazutaka Hirano, Izumiotsu (JP);
Megumi Tomisaki, Izumiotsu (JP);
Akihiro Nabeshima, Tokushima (JP);
Yoshinobu Abe, Tokushima (JP);
Hiroaki Tokuda, Tokushima (JP);
Akinori Oka, Tokushima (JP)

(73) Assignees: Otsuka Chemical Co., Ltd., Osaka (JP);
Stella Chemifa Corporation, Osaka (JP)

( * ) Notice: Subject to any disclaimer, the term of this patent is extended or adjusted under 35 U.S.C. 154(b) by 736 days.

(21) Appl. No.: 11/795,030

(22) PCT Filed: Jan. 12, 2006

(86) PCT No.: PCT/JP2006/300668
§ 371 (c)(1),
(2), (4) Date: Jul. 11, 2007

(87) PCT Pub. No.: WO2006/077895
PCT Pub. Date: Jul. 27, 2006

(65) Prior Publication Data
US 2010/0038578 A1 Feb. 18, 2010

(30) Foreign Application Priority Data
Jan. 12, 2005 (JP) .............................. 2005-005580

(51) Int. Cl.
*H01L 31/04* (2006.01)
*H01G 9/038* (2006.01)

(52) U.S. Cl. ............ 252/62.2; 361/504; 564/285; 564/281; 429/324; 429/330; 429/331; 429/332; 429/338; 429/339; 429/342

(58) Field of Classification Search ............... 252/62.2; 361/504; 564/285, 281; 429/324, 330, 331, 429/332, 338, 339, 342
See application file for complete search history.

(56) References Cited

U.S. PATENT DOCUMENTS

2003/0202316 A1   10/2003   Kawasato et al. ............ 361/502
2004/0094741 A1    5/2004   Sato et al. ...................... 252/1

(Continued)

FOREIGN PATENT DOCUMENTS

EP   1 512 460 A1   3/2005

(Continued)

OTHER PUBLICATIONS

Zhou, Zhi-Bin et al., "Low-melting, Low-viscous, Hydrophobic Ionic Liquids: N-Alkyl(alkyl ether)-N-methylpyrrolidinium Perfluoroethyltrifluoroborate", *Chemistry Letters*, vol. 33, No. 12 (2004) pp. 1636-1637.

*Primary Examiner*—C. Melissa Koslow
(74) *Attorney, Agent, or Firm*—Kubovcik & Kubovcik

(57) ABSTRACT

A quaternary ammonium salt of the formula (1), electrolytic solution and electrochemical device using the salt

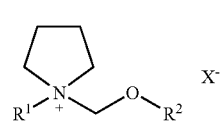

(1)

wherein $R^1$ is straight-chain or branched alkyl having 1 to 4 carbon atoms, $R^2$ is straight-chain or branched alkyl having 1 to 3 carbon atoms, and $X^-$ is $N(CN)_2^-$, $SCN^-$, $NO_3^-$, $NCO^-$ or $NO_2^-$.

8 Claims, 1 Drawing Sheet

U.S. PATENT DOCUMENTS

| | | | |
|---|---|---|---|
| 2007/0042271 A1 | 2/2007 | Nishida et al. | 429/306 |
| 2007/0099079 A1 | 5/2007 | Matsumoto et al. | 429/188 |

FOREIGN PATENT DOCUMENTS

| | | | |
|---|---|---|---|
| JP | 10-55717 A | | 2/1998 |
| JP | 2005-32551 | * | 2/2005 |
| JP | 2005-325052 | * | 11/2005 |

\* cited by examiner

QUATERNARY AMMONIUM SALT, ELECTROLYTE, ELECTROLYTE SOLUTION AND ELECTROCHEMICAL DEVICE

This application is a 371 of international application PCT/JP2006/300668 filed Jan. 12, 2006, which claims priority based on Japanese patent application No. 2005-005580 filed Jan. 12, 2005, which is incorporated herein by reference.

TECHNICAL FIELD

The present invention relates to quaternary ammonium salts, electrolytes, electrolytic solutions and electrochemical devices. More particularly, the invention relates to functional materials which are usable as electrolytes having a high solubility in organic solvents, high electrical conductivity and small in environmental load.

BACKGROUND ART

In recent years, higher power densities and improved energy densities have been required of electrochemical devices including cells and capacitors. Organic electrolytic solutions have found wider use than aqueous electrolytic solutions from the viewpoint of voltage resistance. Examples of organic electrolytic solutions are those prepared by dissolving alkali metal salts or solid ammonium salts in an organic solvent such as propylene carbonate. Electrolytic solutions of the former type are used for lithium ion battery, while those of the latter type are used for electric double-layer capacitor. Organic electrolytic solutions are inferior to aqueous solutions in electrical conductivity, and numerous studies have been made on organic solvents or electrolytes to obtain improved electrical conductivity.

The electrical conductivity of nonaqueous electrolytic solutions comprising such a solid electrolyte dissolved in a solvent varies with the concentration of the electrolyte. With a rise in the concentration, the ion concentration of the solution increases to increase the electrical conductivity, which will reach a maximum in due course. The electrical conductivity reaching the maximum starts to decrease presumably because the electrolyte becomes difficult to dissociate and increases in viscosity at the same time owing to increased interaction between the solvent and ions and between the ions as the number of ions increases in the electrolytic solution. When further increasing in concentration, the electrolyte becomes no longer dissociable, and the concentration of the electrolyte is saturated. Thus, an attempt to increase the concentration of the electrolyte encounters the problem that the electrolyte becomes less soluble. Another problem is also experienced in that when electrolytic solutions having an electrolyte dissolved therein at a high concentration is used in an environment of low temperature, a salt will separate out to impair the electrical conductivity of the solution.

Found in recent years are salts having a melting point around room temperature or salts having a melting point not higher than room temperature (salts melting at room temperature). It is known that even if solid at room temperature, such salts dissolve in organic solvents at a higher concentration than usual electrolytes. Furthermore, the salts melting at room temperature are miscible with a specific organic solvent in a desired ratio. Accordingly, these salts afford electrolytic solutions having a high concentration not available by dissolving conventional solid electrolytes in organic solvents, while although having a high concentration, the solution is less likely to encounter the problem that the salt will separate out in a low-temperature environment. The salt melting at room temperature is itself liquid and is therefore usable singly as an electrolyte.

It is disclosed that aliphatic ammonium salts having an alkoxyalkyl group introduced thereinto are highly soluble in a nonaqueous organic solvent and are less likely to separate out at low temperatures (patent literature 1). However, satisfactory improvements still remain to be made in the electric conductivity of ionic liquids per se, or in the electric conductivity of electrolytic solutions as diluted with an organic solvent.

Many of anions of these electrolytic solutions contain fluorine, chlorine or like halogen. Many halogen-containing anions have high electric conductivity and high voltage resistance but place a heavy burden on the environment. Fluoric anions especially include many which have the drawback of hydrolyzing in the presence of water to produce highly toxic hydrogen fluoride.

[patent literature 1] WO 02/076924

An object of the present invention is to provide an electrolyte which is highly soluble in organic solvents, highly reliable at low temperatures, highly electrically conductive and less likely to burden the environment, and further to provide electrochemical device having such advantages.

DISCLOSURE OF THE INVENTION

The present invention provides the following inventions.

1. A quaternary ammonium salt of the formula (1)

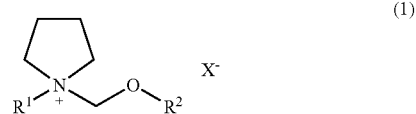

wherein $R^1$ is straight-chain or branched alkyl having 1 to 4 carbon atoms, $R^2$ is straight-chain or branched alkyl having 1 to 3 carbon atoms, and $X^-$ is $N(CN)_2^-$, $SCN^-$, $NO_3^-$, $NCO^-$ or $NO_2^-$.

2. A quaternary ammonium salt of the formula (2)

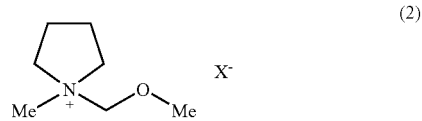

wherein $X^-$ is same as defined above, and Me is methyl.

3. A composition wherein the composition comprises at least one of quaternary ammonium salts of the formula (1) and the formula (2), and an organic solvent.

The present invention provides a quaternary ammonium salt of the formula (1), and an electrolytic solution containing the salt

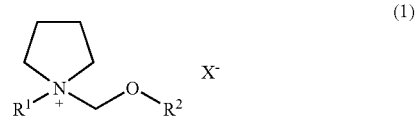

wherein $R^1$ is straight-chain or branched alkyl having 1 to 4 carbon atoms, $R^2$ is straight-chain or branched alkyl having 1 to 3 carbon atoms, and $X^-$ is $N(CN)_2^-$, $SCN^-$, $NO_3^-$, $NCO^-$ or $NO_2^-$.

Examples of straight-chain or branched alkyl having 1 to 4 carbon atoms represented by $R^1$ are methyl, ethyl, n-propyl, iso-propyl, n-butyl, sec-butyl and tert-butyl. Preferable are straight-chain or branched alkyl having 1 to 3 carbon atoms. More preferable are methyl and ethyl.

Examples of straight-chain or branched alkyl having 1 to 3 carbon atoms represented by $R^2$ are methyl, ethyl, n-propyl and iso-propyl. Preferable are methyl and ethyl.

Examples of quaternary ammonium salts of the present invention are N-methoxymethyl-N-methylpyrrolidinium dicyanamide, N-ethyl-N-methoxymethylpyrrolidinium dicyanamide, N-methoxymethyl-N-n-propylpyrrolidinium dicyanamide, N-methoxymethyl-N-iso-propylpyrrolidinium dicyanamide, N-n-butyl-N-methoxymethylpyrrolidinium dicyanamide, N-iso-butyl-N-methoxymethylpyrrolidinium dicyanamide, N-tert-butyl-N-methoxymethylpyrrolidinium dicyanamide, N-methoxymethyl-N-methylpyrrolidinium thiocyanate, N-ethyl-N-methoxymethylpyrrolidinium thiocyanate, N-methoxymethyl-N-n-propylpyrrolidinium thiocyanate, N-methoxymethyl-N-iso-propylpyrrolidinium thiocyanate, N-n-butyl-N-methoxymethylpyrrolidinium thiocyanate, N-iso-butyl-N-methoxymethylpyrrolidinium thiocyanate, N-tert-butyl-N-methoxymethylpyrrolidinium thiocyanate, N-methoxymethyl-N-methylpyrrolidinium nitrate, N-ethyl-N-methoxymethylpyrrolidinium nitrate, N-methoxymethyl-N-n-propylpyrrolidinium nitrate, N-methoxymethyl-N-iso-propylpyrrolidinium nitrate, N-n-butyl-N-methoxymethylpyrrolidinium nitrate, N-iso-butyl-N-methoxymethylpyrrolidinium nitrate, N-tert-butyl-N-methoxymethylpyrrolidinium nitrate, N-methoxymethyl-N-methylpyrrolidinium isocyanate, N-ethyl-N-methoxymethylpyrrolidinium isocyanate, N-methoxymethyl-N-n-propylpyrrolidinium isocyanate, N-methoxymethyl-N-iso-propylpyrrolidinium isocyanate, N-n-butyl-N-methoxymethylpyrrolidinium isocyanate, N-iso-butyl-N-methoxymethylpyrrolidinium isocyanate, N-tert-butyl-N-methoxymethylpyrrolidinium isocyanate, N-methoxymethyl-N-methylpyrrolidinium nitrite, N-ethyl-N-methoxymethylpyrrolidinium nitrite, N-methoxymethyl-N-n-propylpyrrolidinium nitrite, N-methoxymethyl-N-iso-propylpyrrolidinium nitrite, N-n-butyl-N-methoxymethylpyrrolidinium nitrite, N-iso-butyl-N-methoxymethylpyrrolidinium nitrite, N-tert-butyl-N-methoxymethylpyrrolidinium nitrite, N-ethoxymethyl-N-methylpyrrolidinium dicyanamide, N-ethoxymethyl-N-ethylpyrrolidinium dicyanamide, N-ethoxymethyl-N-n-propylpyrrolidinium dicyanamide, N-ethoxymethyl-N-iso-propylpyrrolidinium dicyanamide, N-n-butyl-N-ethoxymethylpyrrolidinium dicyanamide, N-iso-butyl-N-ethoxymethylpyrrolidinium dicyanamide, N-tert-butyl-N-ethoxymethylpyrrolidinium dicyanamide, N-ethoxymethyl-N-methylpyrrolidinium thiocyanate, N-ethoxymethyl-N-ethylpyrrolidinium thiocyanate, N-ethoxymethyl-N-n-propylpyrrolidinium thiocyanate, N-ethoxymethyl-N-iso-propylpyrrolidinium thiocyanate, N-n-butyl-N-ethoxymethylpyrrolidinium thiocyanate, N-iso-butyl-N-ethoxymethylpyrrolidinium thiocyanate, N-tert-butyl-N-ethoxymethylpyrrolidinium thiocyanate, N-ethoxymethyl-N-methylpyrrolidinium nitrate, N-ethoxymethyl-N-ethylpyrrolidinium nitrate, N-ethoxymethyl-N-n-propylpyrrolidinium nitrate, N-ethoxymethyl-N-iso-propylpyrrolidinium nitrate, N-n-butyl-N-ethoxymethylpyrrolidinium nitrate, N-iso-butyl-N-ethoxymethylpyrrolidinium nitrate, N-tert-butyl-N-ethoxymethylpyrrolidinium nitrate, N-ethoxymethyl-N-methylpyrrolidinium isocyanate, N-ethoxymethyl-N-ethylpyrrolidinium isocyanate, N-ethoxymethyl-N-n-propylpyrrolidinium isocyanate, N-ethoxymethyl-N-iso-propylpyrrolidinium isocyanate, N-n-butyl-N-ethoxymethylpyrrolidinium isocyanate, N-iso-butyl-N-ethoxymethylpyrrolidinium isocyanate, N-tert-butyl-N-ethoxymethylpyrrolidinium isocyanate, N-ethoxymethyl-N-methylpyrrolidinium nitrite, N-ethoxymethyl-N-ethylpyrrolidinium nitrite, N-ethoxymethyl-N-n-propylpyrrolidinium nitrite, N-ethoxymethyl-N-iso-propylpyrrolidinium nitrite, N-n-butyl-N-ethoxymethylpyrrolidinium nitrite, N-iso-butyl-N-ethoxymethylpyrrolidinium nitrite, N-tert-butyl-N-ethoxymethylpyrrolidinium nitrite, N-methyl-N-n-propoxymethylpyrrolidinium dicyanamide, N-ethyl-N-n-propoxymethylpyrrolidinium dicyanamide, N-n-propyl-N-n-propoxymethylpyrrolidinium dicyanamide, N-iso-propyl-N-n-propoxymethylpyrrolidinium dicyanamide, N-n-butyl-N-n-propoxymethylpyrrolidinium dicyanamide, N-iso-butyl-N-n-propoxymethylpyrrolidinium dicyanamide, N-tert-butyl-N-n-propoxymethylpyrrolidinium dicyanamide, N-methyl-N-n-propoxymethylpyrrolidinium thiocyanate, N-ethyl-N-n-propoxymethylpyrrolidinium thiocyanate, N-n-propyl-N-n-propoxymethylpyrrolidinium thiocyanate, N-iso-propyl-N-n-propoxymethylpyrrolidinium thiocyanate, N-n-butyl-N-n-proxymethylpyrrolidinium thiocyanate, N-iso-butyl-N-n-propoxymethylpyrrolidinium thiocyanate, N-tert-butyl-N-n-propoxymethylpyrrolidinium thiocyanate, N-methyl-N-n-propoxymethylpyrrolidinium nitrate, N-ethyl-N-n-propoxymethylpyrrolidinium nitrate, N-n-propyl-N-n-propoxymethylpyrrolidinium nitrate, N-iso-propyl-N-n-propoxymethylpyrrolidinium nitrate, N-n-butyl-N-n-propoxymethylpyrrolidinium nitrate, N-iso-butyl-N-n-propoxymethylpyrrolidinium nitrate, N-tert-butyl-N-n-propoxymethylpyrrolidinium nitrate, N-methyl-N-n-propoxymethylpyrrolidinium isocyanate, N-ethyl-N-n-propoxymethylpyrrolidinium isocyanate, N-n-propyl-N-n-propoxymethylpyrrolidinium isocyanate, N-iso-propyl-N-n-propoxymethylpyrrolidinium isocyanate, N-n-butyl-N-n-propoxymethylpyrrolidinium isocyanate, N-iso-butyl-N-n-propoxymethylpyrrolidinium isocyanate, N-tert-butyl-N-n-propoxymethylpyrrolidinium isocyanate, N-methyl-N-n-propoxymethylpyrrolidinium nitrite, N-ethyl-N-n-propoxymethylpyrrolidinium nitrite, N-n-propyl-N-n-propoxymethylpyrrolidinium nitrite, N-iso-propyl-N-n-propoxymethylpyrrolidinium nitrite, N-n-butyl-N-n-propoxymethylpyrrolidinium nitrite, N-iso-butyl-N-n-propoxymethylpyrrolidinium nitrite, N-tert-butyl-N-n-propoxymethylpyrrolidinium nitrite, N-methyl-N-iso-propoxymethylpyrrolidinium dicyanamide, N-ethyl-N-iso-propoxymethylpyrrolidinium dicyanamide, N-n-propyl-N-iso-propoxymethylpyrrolidinium dicyanamide, N-iso-propyl-N-iso-propoxymethylpyrrolidinium dicyanamide, N-n-butyl-N-iso-propoxymethylpyrrolidinium dicyanamide, N-iso-butyl-N-iso-propoxymethylpyrrolidinium dicyanamide, N-tert-butyl-N-iso-propoxymethylpyrrolidinium dicyanamide, N-methyl-N-iso-propoxymethylpyrrolidinium thiocyanate, N-ethyl-N-iso-propoxymethylpyrrolidinium thiocyanate, N-n-propyl-N-iso-propoxymethylpyrrolidinium thiocyanate, N-iso-propyl-N-iso-propoxymethylpyrrolidinium thiocyanate, N-n-butyl-N-iso-propoxymethylpyrrolidinium thiocyanate, N-iso-butyl-N-iso-propoxymethylpyrrolidinium thiocyanate, N-tert-butyl-N-iso-propoxymethylpyrrolidinium thiocyanate, N-methyl-N- iso-propoxymethylpyrrolidinium nitrate, N-ethyl-N-iso-propoxymethylpyrrolidinium nitrate, N-n-propyl-N-iso-propoxymethylpyrrolidinium nitrate, N-iso-propyl-N-iso-propoxymethylpyrrolidinium nitrate, N-n-butyl-N-iso-propoxymethylpyrrolidinium nitrate, N-iso-butyl-N-iso-propoxymethylpyrrolidinium nitrate, N-tert-butyl-N-iso-propoxymethylpyrrolidinium nitrate, N-methyl-N-iso-propoxymethylpyrrolidinium isocyanate, N-ethyl-N-iso-propoxymethylpyrrolidinium isocyanate, N-n-propyl-N-iso-propoxymethylpyrrolidinium isocyanate, N-iso-propyl-N-iso-propoxymethylpyrrolidinium isocyanate, N-n-butyl-N-iso-propoxymethylpyrrolidinium isocyanate, N-iso-butyl-N-iso-propoxymethylpyrrolidinium isocyanate, N-tert-butyl-N-iso-propoxymethylpyrrolidinium isocyanate, N-methyl-N-iso-propoxymethylpyrrolidinium nitrite, N-ethyl-N-iso-propoxymethylpyrrolidinium nitrite, N-n-propyl-N-iso-propoxymethylpyrrolidinium nitrite, N-iso-propyl-N-iso-propoxymethylpyrrolidinium nitrite, N-n-butyl-N-iso-propoxymethylpyrrolidinium nitrite, N-iso-butyl-N-iso-propoxymethylpyrrolidinium nitrite and N-tert-butyl-N-iso-propoxymethylpyrrolidinium nitrite.

Preferable are N-methoxymethyl-N-methylpyrrolidinium dicyanamide, N-ethyl-N-methoxymethylpyrrolidinium dicyanamide, N-ethoxymethyl-N-methylpyrrolidinium dicyanamide and N-ethoxymethyl-N-ethylpyrrolidinium dicyanamide.

Preferable are N-methoxymethyl-N-methylpyrrolidinium thiocyanate, N-ethyl-N-methoxymethylpyrrolidinium thiocyanate, N-ethoxymethyl-N-methylpyrrolidinium thiocyanate and N-ethoxymethyl-N-ethylpyrrolidinium thiocyanate.

Preferable are N-methoxymethyl-N-methylpyrrolidinium nitrate, N-ethyl-N-methoxymethylpyrrolidinium nitrate, N-ethoxymethyl-N-methylpyrrolidinium nitrate and N-ethoxymethyl-N-ethylpyrrolidinium nitrate.

Preferable are N-methoxymethyl-N-methylpyrrolidinium isocyanate, N-ethyl-N-methoxymethylpyrrolidinium isocyanate, N-ethoxymethyl-N-methylpyrrolidinium isocyanate and N-ethoxymethyl-N-ethylpyrrolidinium isocyanate.

Preferable are N-methoxymethyl-N-methylpyrrolidinium nitrite, N-ethyl-N-methoxymethylpyrrolidinium nitrite, N-ethoxymethyl-N-methylpyrrolidinium nitrite and N-ethoxymethyl-N-ethylpyrrolidinium nitrite.

More preferable are N-methoxymethyl-N-methylpyrrolidinium dicyanamide and N-ethoxymethyl-N-methylpyrrolidinium dicyanamide.

More preferable are N-methoxymethyl-N-methylpyrrolidinium thiocyanate and N-ethoxymethyl-N-methylpyrrolidinium thiocyanate.

More preferable are N-methoxymethyl-N-methylpyrrolidinium nitrate and N-ethoxymethyl-N-methylpyrrolidinium nitrate.

More preferable are N-methoxymethyl-N-methylpyrrolidinium isocyanate and N-ethoxymethyl-N-methylpyrrolidinium isocyanate, More preferable are N-methoxymethyl-N-methylpyrrolidinium nitrite and N-ethoxymethyl-N-methylpyrrolidinium nitrite, The quaternary ammonium salt of the present invention can be prepared by various processes. Typical of these processes are represented by Equation-1 and Equation-2 given below.

Preparation of Process of Equation-1

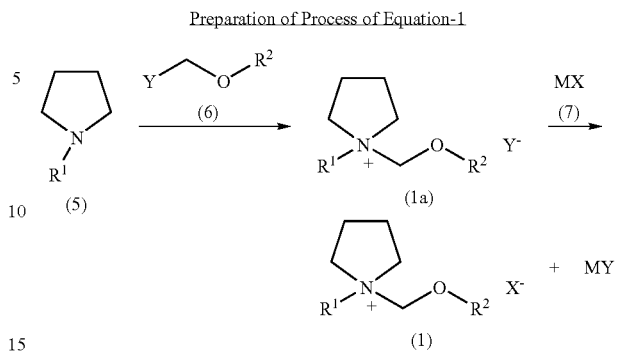

An alkylpyrrolidine of the formula (5) wherein $R^1$ is the same as above is reacted with a compound of the formula (6) wherein $R^2$ is the same as above, and Y is Cl, Br, I or the like to prepare a quaternary ammonium salt of the formula (1a), which is then subjected to salt-exchange reaction with a compound of the formula (7) to prepare a quaternary ammonium salt of the formula (1) Represented by M in the formula (7) is one of atoms including hydrogen, alkali metal atoms such as Na, K and Li, alkaline earth metal atoms such as Ca, Mg and Ba, and metal atoms such as Ag.

The tertiary amine of the formula (5) serving as the starting material and the compound of the formula (6) are both known substances. Examples of tertiary amine of the formula (5) are methylpyrrolidine, ethylpyrrolidine, n-propylpyrrolidine, isopropylpyrrolidine, n-butylpyrrolidine, isobutylpyrrolidine, tert-butylpyrrolidine, etc.

Examples of compounds of the formula (6) are chloromethyl methyl ether, bromomethyl methyl ether, iodomethyl methyl ether, chloromethyl ethyl ether, bromomethyl ethyl ether, iodomethyl ethyl ether, chloromethyl n-propyl ether, bromomethyl n-propyl ether, iodomethyl n-propyl ether, chloromethyl iso-propyl ether, bromomethyl iso-propyl ether, iodomethyl iso-propyl ether, etc.

The tertiary amine of the formula (5) and the compound of the formula (6) are reacted in a suitable solvent.

The solvent to be used can be a wide variety of known solvents insofar as they are capable of solving the tertiary amine of the formula (5) and the compound of the formula (6) and will not adversely affect the reaction. Examples of such solvents are benzene, toluene, xylene and like aromatic hydrocarbons, dichloromethane, chloroform, carbon tetrachloride and like hydrocarbon halides, methanol, ethanol, isopropanol, n-butanol, tert-butanol and like lower alcohols, acetone, methyl ethyl ketone and like ketones, diethyl ether, diisopropyl ether and like ethers, methyl acetate, ethyl acetate, butyl acetate and like esters, n-hexane, n-heptane and like aliphatic hydrocarbons, cyclohexane and like aliphatic hydrocarbons, etc. Preferable among these solvents are toluene and like aromatic hydrocarbons, chloroform and like hydrocarbon halides, acetone and like ketones and methyl acetate and like esters. These solvents can be used singly, or at least two of them are usable in admixture. Preferable to use are solvents which are free from water (up to 1000 ppm in water content).

The tertiary amine of the formula (5) and the compound of the formula (6) are used in the ratio usually of 0.5 to 5 moles, preferably 0.9 to 1.2 moles, of the latter per mole of the former.

The reaction is carried out usually at −30 to 100° C., more particularly at −10 to 40° C. The reaction is completed generally in several hours to about 24 hours.

The reaction of the quaternary ammonium salt of the formula (1a) obtained above with the compound of the formula (7) is carried out by a usual salt exchange reaction.

The compound of the formula (7) used as a starting material is a known compound. Examples of these are $HN(CN)_2$, $LiN(CN)_2$, $NaN(CN)_2$, $KN(CN)_2$, $AgN(CN)_2$, HSCN, LiSCN, NaSCN, KSCN, AgSCN, $HNO_3$, $LiNO_3$, $NaNO_3$, $KNO_3$, $AgNO_3$, HNCO, LiNCO, NaNCO, KNCO, AgNCO, $HNO_2$, $LiNO_2$, $NaNO_2$, $KNO_2$ and $AgNO_2$.

This salt exchange reaction is carried out in a suitable solvent. The solvent to be used can be a wide variety of known solvents insofar as they are capable of dissolving the quaternary ammonium salt of the formula (1a) and the compound of the formula (7) and will not adversely affect the reaction. Examples of such solvents are water, dichloromethane, chloroform, carbon tetrachloride and like hydrocarbon halides, methanol, ethanol, isopropanol, n-butanol, tert-butanol and like lower alcohols, acetone, methyl ethyl ketone and like ketones, ethyl acetate, butyl acetate and like esters, dimethyl sulfoxide, dimethylformamide and like aprotic polar solvents. Preferable among these are methanol and like lower alcohols, chloroform and like hydrocarbon halides and water. These solvents are usable singly, or at least two of them are usable in admixture.

The quaternary ammonium salt of the formula (1a) and the compound of the formula (7) are used in the ratio usually of 0.3 to 5 moles, preferably 0.9 to 1.2 moles, of the latter per mole of the former.

The reaction proceeds usually rapidly, so that a solution of the two reactants as dissolved in a solvent is reacted at 5 to 150° C. for about 10 minutes to about 24 hours.

The desired products obtained by the foregoing respective reactions can each be readily isolated from the reaction mixture and purified by usual isolating and purifying means such as centrifuging, concentration, washing, organic solvent extraction, chromatography and recrystallization.

The salt exchange reaction can be carried out with use of an ion-exchange resin. Examples of the ion-exchange resin are anion-exchange resin. The salt exchange reaction is performed by exchanging anions in the resin into desired anions and then passing into the resin a solution dissolved therein the quaternary ammonium salt of the formula (1a). The solvent to be used can be a wide variety of known solvents insofar as they are capable of dissolving the salt of the formula (1a) and will not adversely affect the reaction. Examples of such solvents are water and alcohols.

In the case where the product is to be placed into use in which the presence of halogen in the product is objectionable, the amount of halogen present can be diminished by subjecting the halogen salt to neutralization or salt exchange, and further converting the product into a salt in conformity with the contemplated use. Examples of useful neutralizing agents are alkali metal salts, alkaline earth metal salts, organic alkali metal salts, silver salts, etc. More specific examples of such agents are sodium carbonate, potassium carbonate, lithium carbonate, calcium carbonate, sodium hydroxide, potassium hydroxide, lithium hydroxide, calcium hydroxide, sodium perchlorate, potassium perchlorate, lithium perchlorate, sodium acetate, potassium acetate, silver sulfate, silver nitrate, silver perchlorate, etc.

The reaction can be carried out in the same mode as the procedure for preparing the quaternary ammonium salt of the formula (1). The procedure for preparing the quaternary ammonium salt of the formula (1) is usable also as the subsequent procedure for converting the dehalogenated salt into a salt in conformity with the contemplated use.

Stated specifically, the quaternary ammonium salt of the formula (1) wherein X is $N(CN)_2$ is prepared from a quaternary ammonium salt of the formula (1a) by the reaction procedure to be described below.

The quaternary ammonium salt of the formula (1a) is dissolved in water, and a specified amount of silver dicyanamide is added to the solution to conduct a reaction at 5 to 150° C. for about 10 hours. The silver halide or the like is filtered off, and the filtrate is concentrated in a vacuum and dried, whereby the desired compound can be isolated. It is preferable to pass the filtrate through an alumina column to remove impurities such as very small amount of silver dicyanamide.

Preparartion process of Equation-2

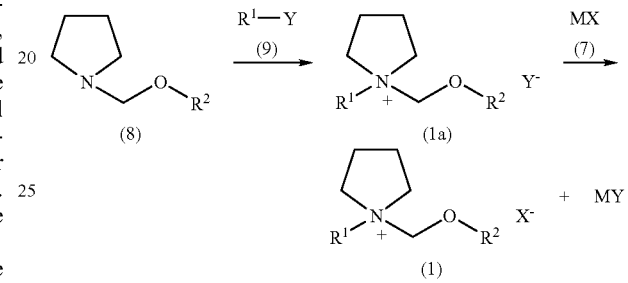

An alkoxypyrrolidine of the formula (8) wherein $R^2$ is the same as above is reacted with a compound of the formula (9) wherein $R^1$ and Y are the same as above to prepare a quaternary ammonium salt of the formula (1a), which is then reacted with a compound of the formula (7) wherein M and X are the same as above to thereby prepare a quaternary ammonium salt of the formula (1) by salt exchange reaction. Represented by M in the formula (7) is one of atoms including hydrogen, alkali metal atoms such as Na, K and Li, alkaline earth metal atoms such as Ca, Mg and Ba, and metal atoms such as Ag.

The alkoxypyrrolidine of the formula (8) serving as the starting material and the compound of the formula (9) are both known substances.

The alkoxypyrrolidine of the formula (8) is prepared by known processes. Such processes are disclosed, for example, in C. M. McLeod und G. M. Robinson, J. Chem. Soc. 119, 1470(1921), G. M. Robinson und R. Robinson, J. Chem. Soc. 123, 532(1923), Stewert, T. D.; Bradly, W. E., J. Am. Chem. Soc. 1932, 54, 4172-4183.

The alkoxypyrrolidine of the formula (8) is prepared generally by using pyrrolidine, formaldehyde or p-formaldehyde, alcohol, and alkali carbonate. Used per mole of pyrrolidine are 0.5 to 3.0 moles, preferably 0.6 to 1.5 moles of 10 to 38 wt % aqueous solution of formaldehyde or p-formaldehyde, 0.5 to 3.0 moles, preferably 2.0 to 3.0 moles of an alcohol, and 0.2 to 3.0 moles, preferably 0.4 to 1.0 mole of an alkali carbonate. The reaction is carried out at a temperature of −5 to 25° C. when aqueous solution of formaldehyde is used, and 60 to 100° C. when aqueous solution of p-formaldehyde is used, and is completed in several hours to about 24 hours. The alkoxypyrrolidine of the formula (8) can be readily isolated from the reaction mixture and purified by usual isolating means such as extraction and rectification.

Examples of the compound of the formula (9) are methyl chloride, methyl bromide, methyl iodide, ethyl chloride, ethyl iodide, ethyl bromide, n-propyl chloride, n-propyl bromide, n-propyl iodide, iso-propyl chloride, iso-propyl bromide, iso-propyl iodide, n-butyl chloride, n-butyl bromide, n-butyl iodide, iso-butyl chloride, iso-butyl bromide, iso-butyl iodide, tert-butyl chloride, tert-butyl bromide and tert-butyl iodide.

The alkoxypyrrolidine of the formula (8) is reacted with the compound of the formula (9) in a suitable solvent.

The solvent to be used can be a wide variety of those already known insofar as they are capable of dissolving the alkoxypyrrolidine of the formula (8) and the compound of the formula (9) and will not adversely affect the reaction. Examples of such solvents are benzene, toluene, xylene and like aromatic hydrocarbons, dichloromethane, chloroform, carbon tetrachloride and like hydrocarbon halides, methanol, ethanol, isopropanol, n-butanol, tert-butanol and like lower alcohols, acetone, methyl ethyl ketone and like ketones, diethyl ether, diisopropyl ether and like ethers, methyl acetate, ethyl acetate, butyl acetate and like esters, n-hexane, n-heptane and like aliphatic hydrocarbons, cyclohexane and like aliphatic hydrocarbons, etc. Preferable among these solvents are acetone and like ketone, toluene and like aromatic hydrocarbons, and chloroform and like hydrocarbon halides. These solvents can be used singly, or at least two of them are usable in admixture. Especially preferable to use are solvents which are free from water (up to 1000 ppm in water content).

The alkoxypyrrolidine of the formula (8) and the compound of the formula (9) are used in the ratio usually of 0.5 to 5 moles, preferably 0.9 to 1.2 moles, of the latter per mole of the former.

The reaction is carried out usually at 0 to 150° C. The reaction is completed generally in about 24 hours to about 72 hours. When an alkyl halide having a low boiling point is used for producing the quaternary salt, it is desirable to use an autoclave.

The reaction of the quaternary ammonium salt of the formula (1a) obtained above with the compound of the formula (7) is carried out by a usual salt exchange reaction.

The compound of the formula (7) serving as the starting material is a known compound. Examples of thereof are $HN(CN)_2$, $LiN(CN)_2$, $NaN(CN)_2$, $KN(CN)_2$, $AgN(CN)_2$, HSCN, LiSCN, NaSCN, KSCN, AgSCN, $HNO_3$, $LiNO_3$, $NaNO_3$, $KNO_3$, $AgNO_3$, HNCO, LiNCO, NaNCO, KNCO, AgNCO, $HNO_2$, $LiNO_2$, $NaNO_2$, $KNO_2$ and $AgNO_2$.

This salt exchange reaction is carried out in a suitable solvent. The solvent to be used can be a wide variety of known solvents insofar as they are capable of dissolving the quaternary ammonium salt of the formula (1a) and the compound of the formula (7) and will not adversely affect the reaction. Examples of such solvents are water, dichloromethane, chloroform, carbon tetrachloride and like hydrocarbon halides, methanol, ethanol, isopropanol, n-butanol, tert-butanol and like lower alcohols, acetone, methyl ethyl ketone and like ketones, ethyl acetate, butyl acetate and like esters, dimethyl sulfoxide, dimethylformamide and like aprotic polar solvents. Preferable among these are methanol and like lower alcohols, chloroform and like hydrocarbon halides and water. These solvents are usable singly, or at least two of them are usable in admixture.

The quaternary ammonium salt of the formula (1a) and the compound of the formula (7) are used in the ratio usually of 0.3 to 5 moles, preferably 0.9 to 1.2 moles, of the latter per mole of the former. The reaction proceeds usually rapidly, so that a solution of the two reactants in a solvent is reacted at about 5 to about 150° C. for about 10 minutes to about 24 hours.

The desired products obtained by the foregoing respective reactions can each be readily isolated from the reaction mixture and purified by usual isolating and purifying means such as centrifuging, concentration, washing, organic solvent extraction, chromatography and recrystallization.

The salt exchange reaction can also be carried out with use of an ion-exchange resin. Examples of the ion-exchange resin are anion-exchange resin. The salt exchange reaction is performed by exchanging anions in the resin into desired anions and then passing into the resin a solution dissolved therein the quaternary ammonium salt of the formula (1a). The solvent to be used can be a wide variety of known solvents insofar as they are capable of dissolving the salt of the formula (1a) and will not adversely affect the reaction. Examples of such solvents are water and alcohols.

In the case where the product is to be placed into use in which the presence of halogen in the product is objectionable, the amount of halogen present can be diminished by subjecting the halogen salt to neutralization or salt exchange, and further converting the product into a salt in conformity with the contemplated use. Examples of useful neutralizing agents are alkali metal salts, alkaline earth metal salts, organic alkali metal salts, silver salts, etc. More specific examples of such agents are sodium carbonate, potassium carbonate, lithium carbonate, calcium carbonate, sodium hydroxide, potassium hydroxide, lithium hydroxide, calcium hydroxide, sodium perchlorate, potassium perchlorate, lithium perchlorate, sodium acetate, potassium acetate, silver sulfate, silver nitrate, silver perchlorate, etc.

The reaction can be carried out in the same mode as the procedure for preparing the quaternary ammonium salt of the formula (1). The procedure for preparing the quaternary ammonium salt of the formula (1) is usable also as the subsequent procedure for converting the dehalogenated salt into a salt in conformity with the contemplated use.

Stated specifically, the quaternary ammonium salt of the formula (1) wherein X is $N(CN)_2$ is prepared from a quaternary ammonium salt of the formula (1a) by the reaction procedure to be described below.

The quaternary ammonium salt of the formula (1a) is dissolved in water, and a specified amount of silver dicyanamide is added to the solution to conduct a reaction at 5 to 150° C. for about 10 hours. The silver halide or the like is filtered off, and the filtrate is concentrated in a vacuum and dried, whereby the desired compound can be isolated. It is preferable to pass the filtrate through an alumina column to remove impurities such as very small amount of silver dicyanamide.

The quaternary ammonium salt of the formula (1) contains water in an amount of preferably up to 100 ppm, more preferably up to 50 ppm, further more preferably up to 30 ppm, especially most preferably up to 10 ppm. When the quaternary ammonium salt of the formula (1) of the invention itself is a liquid at room temperature, the salt is usable as it is as an electrolytic solution. These salts are usable singly, or at least two of them are usable in admixture.

The quaternary ammonium salt of the formula (1) of the invention is usable as an electrolytic solution as mixed with a suitable organic solvent. Also these salts are usable singly, or at least two of them are usable in admixture.

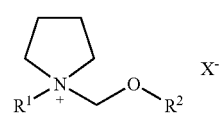

(1)

Examples of organic solvents are cyclic carbonic acid esters, chain carbonic acid esters, phosphoric acid esters, cyclic ethers, chain ethers, lactone compounds, chain esters, nitrile compounds, amide compounds, sulfone compounds, etc. These solvents may be used singly, or at least two of them are usable in admixture.

Although not limitative, the solvents given below are more specific examples of useful solvents.

Examples of cyclic carbonic acid esters are ethylene carbonate, propylene carbonate, butylene carbonate, etc. Preferable is propylene carbonate.

Examples of chain carbonic acid esters are dimethyl carbonate, ethylmethyl carbonate, methyl-n-propyl carbonate, methyl-isopropyl carbonate, n-butylmethyl carbonate, diethyl carbonate, ethyl-n-propyl carbonate, ethyl-iso-propyl carbonate, n-butylethyl carbonate, di-n-propyl carbonate, di-iso-propyl carbonate and di-n-butyl carbonate. Preferable are dimethyl carbonate and ethylmethyl carbonate.

Examples of phosphoric acid esters are trimethyl phosphate, triethyl phosphate, ethyldimethyl phosphate, diethylmethyl phosphate, etc.

Examples of cyclic ethers are tetrahydrofuran, 2-methyltetrahydrofuran, etc.

Examples of chain ethers are dimethoxyethane, etc.

Examples of lactone compounds are gamma-butyrolactone and the like.

Examples of chain esters are methyl propionate, methyl acetate, ethyl acetate, methyl formate, etc.

Examples of nitrile compounds are acetonitrile and the like.

Examples of amide compounds are dimethylformamide and the like.

Examples of sulfone compounds are sulfolane, methyl sulfolane, etc.

Preferable are cyclic carbonic acid esters, chain carbonic acid esters, nitrile compounds and sulfone compounds.

These solvents may be used singly, or at least two of them are usable in admixture.

Examples of mixtures of solvents are a mixture of cyclic carbonic acid ester and chain carbonic acid ester, a mixture of chain carbonic acid ester and chain carbonic acid ester and a mixture of sulfolane compound and sulfolane compound.

Examples of mixtures of cyclic carbonic acid ester and chain carbonic acid ester are ethylene carbonate and dimethyl carbonate; ethylene carbonate and ethylmethyl carbonate; ethylene carbonate and diethyl carbonate; propylene carbonate and dimethyl carbonate; propylene carbonate and ethylmethyl carbonate; propylene carbonate and diethyl carbonate; etc.

Examples of mixtures of chain carbonic acid ester and chain carbonic acid ester are dimethyl carbonate and ethylmethyl carbonate.

Examples of mixtures of sulfolane compound and sulfolane compound are sulfolane and methyl sulfolane.

Preferable examples of mixtures are ethylene carbonate and ethylmethyl carbonate; propylene carbonate and ethylmethyl carbonate; dimethyl carbonate and ethylmethyl carbonate; etc.

When the electrolyte of the quaternary ammonium salt of the formula (1) of the invention is used as dissolved in an organic solvent, the concentration of the electrolyte is at least 0.1 M, preferably at least 0.5 M and more preferably at least 1 M.

The quaternary ammonium salt of the formula (1) of the invention or a solution of such a salt as dissolved in an organic solvent is usable as an electrolytic solution for electrochemical devices.

Examples of electrochemical devices are electric double-layer capacitors and secondary cells.

Electrolyte or electrolytic solution of the invention is usable as those used in known electrolytes or electrolytic solutions for electric double-layer capacitors or secondary batteries.

When the electrolyte of the quaternary ammonium salt of the formula (1) of the invention is used as dissolved in an organic solvent for electrolytic solutions of electrochemical devices, the concentration of the electrolyte is at least 0.1 M, preferably at least 0.5 M and more preferably at least 1 M. If the concentration is lower than 0.1 M, the solution is low in electrical conductivity, providing electrochemical devices of impaired performance. The upper limit concentration is the concentration permitting the quaternary ammonium salt to separate from the organic solvent when the salt is liquid at room temperature. If the salt is free of separation, the upper limit concentration is 100%. When the quaternary ammonium salt is solid at room temperature, the concentration at which the organic solvent becomes saturated with the salt is the upper limit concentration.

An electrolytic solution for electrochemical devices can be prepared using the quaternary ammonium salt of the formula (1) of the invention. The electrolytic solution obtained by the invention is usable for electrochemical devices wherein electric energy can be stored by a physical activity or chemical activity and can be used suitably for example in electric double-layer capacitor and lithium batteries.

A description will be given of a method of preparing an electrolytic solution for use in electric double-layer capacitor using the quaternary ammonium salt of the formula (1) of the invention. When the quaternary ammonium salt of the formula (1) of the invention itself is a liquid, the salt is usable as it is as an electrolytic solution, while the salt may be used as mixed with a suitable organic solvent. In preparing electrolytic solution for use in electric double-layer capacitor, since water adversely affects the performance of electric double-layer capacitors, it is desirable to conduct the work free from the atmospheric air, for example, within a glove box having an inert atmosphere of argon or nitrogen. The water content of the work environment can be controlled using a dewpoint meter and is preferably up to minus 60° C. When the work environment is in excess of minus 60° C. and if the work is carried out over a prolonged period of time, the electrolyte or electrolytic solution will absorb water from the atmosphere and therefore rises in water content. The water content of the electrolyte or electrolytic solution can be measured by a Karl Fischer moisture meter.

In the case where a solution of the quaternary ammonium salt of the formula (1) of the invention in an organic solvent is to be used as the electrolytic solution of electrochemical devices, the concentration of the electrolyte is preferably at least 0.1 M, more preferably at least 0.5 M, especially preferably at least 1 M. The upper limit concentration is not defined insofar as no precipitation or separation of the electrolyte occurs.

Examples of organic solvents to be used are various as previously mentioned, whereas since the properties such as dielectric constant, viscosity and melting point differ depending on the combination of the quaternary ammonium salt of the invention and the kind of solvent to be mixed therewith, it is desirable to determine the composition of the mixture in accordance with the combination of the quaternary ammonium salt of the formula (1) of the invention and the solvent to be mixed therewith for use.

For example, in the case of an electrolytic solution comprising N-methoxymethyl-N-methylpyrrolidinium dicyanamide and propylene carbonate, the solution comprises preferably 30 to 80 wt. %, more preferably 40 to 80 wt. % of the dicyanamide. In the case of an electrolytic solution comprising N-methoxymethyl-N-methylpyrrolidinium dicyanamide and acetonitrile, the solution comprises preferably 20 to 80 wt. %, more preferably 40 to 60 wt. % of the dicyanamide.

The quaternary ammonium salt of the formula (1) of the invention is usable as an electrolytic solution also for secondary batteries, especially for lithium secondary batteries. Since water adversely affects the characteristics of lithium batteries as when the electrolytic solution of electric double-layer capacitor is prepared, the solution is prepared preferably within a glove box having its dewpoint controlled.

In the case where the quaternary ammonium salt of the formula (1) of the invention itself is a liquid, the salt is usable as an electrolytic solution when having a lithium salt dissolved therein. Alternatively, the quaternary ammonium salt of the formula (1) of the invention is admixed with a suitable organic solvent, and a lithium salt is dissolved in the mixture for use as an electrolytic solution. Examples of the lithium salts are lithium hexafluorophosphate lithium borofluoride, lithium perchlorate, lithium trifluoromethanesulfonate, lithium sulfonylimide and lithium sulfonylmethide. The lithium salt to be used can be a wide variety of salts and is not limited particularly insofar as the solution is free of separation of the salt.

The concentration of the lithium salt is usually 0.1 to 2.0 moles, preferably 0.15 to 1.5 moles, more preferably 0.2 to 1.2, especially preferably 0.3 to 1.0 moles. If the concentration is less than 0.1 mole and when the charge-discharge rate is great, depletion of lithium ion occurs in the vicinity of the electrode to result in impaired charge-discharge characteristics. If the lithium ion concentration is over 2.0 moles, the electrolytic solution has a high viscosity to entail lower electrical conductivity.

The quaternary ammonium salt is usable as an electrolytic solution as mixed with a suitable organic solvent. Also these salts are usable singly, or at least two of them are usable in admixture.

Examples of organic solvents are same as those stated above and are cyclic carbonic acid esters, chain carbonic acid esters, phosphoric acid esters, cyclic ethers, chain ethers, lactone compounds, chain esters, nitrile compounds, amide compounds, sulfone compounds, etc. These solvents may be used singly, or at least two of them are usable in admixture.

It is desired that the electrolytic solution to be used in the present invention contain at least one of specific organic additives. Examples of specific organic additives are ethylene carbonate, vinylene carbonate, butylene carbonate, ethylene trithiocarbonate, vinylene trithiocarbonate and ethylene sulfite. Preferable are ethylene carbonate and vinylene carbonate. These additives may be used singly, or at lest two of them are usable in admixture. The organic additive incorporated into the solution forms on the surface of the negative electrode of the lithium cell a film known as SEI (solid electrolyte interface) for lithium ions to permeate therethrough selectively, inhibiting the decomposition of ammonium cations which form the quaternary ammonium salt or insertion of ammonium cations into the negative electrode material and consequently giving stabilized charge-discharge characteristics. Some kinds of such organic additives are substances also having the function of a diluting organic solvent.

The organic additive is used preferably in a proportion preferably of 1 to 40 wt. %, more preferably 1 to 30 wt. %, further more preferably 1 to 20 wt. %, most preferably 1 to 10 weight %, based on the weight of the entire electrolytic solution. If the proportion is less than 1 wt. %, a satisfactory film will not be formed over the surface of the negative electrode, permitting the decomposition of ammonium cations which form the quaternary ammonium salt or insertion of ammonium cations into the negative electrode material.

Electric double layer capacitor can be favorably fabricated using the electrolytic solution of the invention thus obtained.

FIG. 1 shows an example of electric double layer capacitor. Electric double layer capacitors are not limited to those of coin shape as shown in FIG. 1. Such a capacitor may be in the form of an assembly of superposed electrodes as placed in a can, a roll of electrodes as wound up and placed in a can, or a so-called laminate as packaged in an aluminum laminate. A description will be given of the structure of the coin-shaped electric double layer capacitor as an example.

FIG. 1 is a diagram showing the coin-shaped electric double layer capacitor in section. Electrodes 1, 2 are arranged as opposed to each other with a separator interposed therebetween, and are housed in container members 4, 5. The electrode comprises a polarizable electrode portion made of a carbon material such as activated carbon, and a current collector portion. The container members 4, 5 need only to be free of corrosion with the electrolytic solution and are made, for example, from stainless steel, aluminum or the like. The container members 4, 5 are electrically insulated with an insulation gasket 6, which also hermetically seals off the interior of a metal container to prevent water and air from ingressing into the interior from outside the container. The current collector of the electrode 1 and the container member 4, as well as the current collector of the electrode 2 and a metal spacer 7, are held in contact with each other under suitable pressure by the presence of a metal spring 8, and are thereby electrically connected. To ensure enhanced electric conductivity, the current collector may be adhered with a carbon paste or like conductive paste.

The polarizable electrode is made preferably from a material having a great specific surface area and high electric conductivity. The material needs to be electrochemically stable to the electrolytic solution within the range of voltages to be applied for use. Examples of such materials are carbon materials, metal oxide materials, conductive high-molecular-weight materials, etc. In view of the cost, the material for the polarizable electrode is preferably carbon material.

Activated carbon materials are desirable as carbon materials. Examples of such materials are sawdust activated carbon, coconut shell activated carbon, pitch or coke activated carbon, phenolic resin activated carbon, polyacrylonitrile activated carbon, celluosic activated carbon, etc.

Examples of metal oxide materials usable are ruthenium oxide, manganese oxide, cobalt oxide, etc.

Examples of conductive high-molecular-weight materials to be used are polyaniline, polypyrrole film, polythiophene film, poly(3,4-ethylenedioxythiophene) film, etc.

The electrode can be obtained by molding the polarizable electrode material and a binder by press work, or by admixing the polarizable electrode material with a binder and an organic solvent such as pyrrolidine to prepare a paste, coating aluminum foil or like current collector with the paste and drying the coated current collector.

Preferably, the separator has high electron insulating properties, is highly wettable with the electrolytic solution and highly permeable to ions, and needs to be electrochemically stable within the range of voltages to be applied. Although the material for the separator is not limited particularly, it is suitable to use paper made from rayon, Manila hemp or the like, porous polyolefin film, nonwoven polyethylene fabric, nonwoven polypropylene fabric, etc.

The electrolytic solution according to the invention and thus prepared is suitable for use in fabricating lithium secondary batteries. The lithium secondary battery of the invention is, for example, in the form of a coin, hollow cylinder, square or rectangle or laminate. FIG. 2 shows a coin-shaped battery as an example of lithium secondary cell.

The lithium secondary battery will be described below based on FIG. 2.

Into internal space defined by a positive electrode can 14 and a negative electrode can 15 are placed a positive electrode 11, separator 13, negative electrode 12 and spacer 17 in this order to provide a stack of superposed layers as positioned on the positive electrode can 14. A spring 18 is interposed between the negative electrode can 15 and the spacer 17 to press the positive electrode 11 and the negative electrode 12 against each other and fixedly position the electrodes in place. The assembly of positive electrode 11, separator 13 and negative electrode 12 is impregnated with the electrolytic solution. With a gasket 16 provided between the positive and negative cans 14, 15, the two cans 14 and 15 are joined by crimping, whereby the stack of components is enclosed as sealed off.

Examples of positive electrode active substances are composite oxides of lithium and transition metal or metals, such as $LiCoO_2$, $LiNiO_2$, $LiNi_{1-x}Co_xO_2$, $LiNi_{1-y-z}Co_yMn_zO_2$, $LiNi_{0.5}Mn_{0.50}O_2$, $LiMnO_2$, $LiMn_2O_4$ and $LiNi_{0.5}Mn_{1.5}O_4$, oxides such as $TiO_2$ and $V_2O_5$, sulfides such as $TiS_2$ and FeS, etc. From the viewpoint of cell capacity and energy density, composite oxides of lithium and transition metal or metals are desirable.

In the above, $1>x>0$, $1>y>0$, $1>z>0$, $y+z<1$. Such a positive electrode active substance can be molded into a positive electrode along with known auxiliary conductive agent and binder under pressure. Alternatively, the positive electrode can be made by mixing the positive electrode active substance with pyrrolidine or like organic solvent along with known conductive agent and binder to prepare a paste, coating a current collector of aluminum foil with the paste and drying the coating.

Examples of negative electrode active substances are a metal lithium, alloy of metal lithium and other metal, and a material for lithium ions to be inserted thereinto and to be released therefrom. Examples of alloys of metal lithium and other metals are Li—Al, Li—Sn, Li—Zn, Li—Si, etc. Examples of materials for lithium ions to be inserted thereinto and to be released therefrom are carbon materials prepared by firing a resin or pitch, a carbon material obtained by adding a boron compound to such a carbon material, natural graphite, etc. These negative electrode materials can be used singly, or at least two of them are usable in admixture.

Such a negative electrode material can be molded into a negative electrode along with known auxiliary conductive agent and binder under pressure. Alternatively, the negative electrode can be made by mixing the negative electrode active substance with pyrrolidone or like organic solvent along with known conductive agent and binder to prepare a paste, coating a current collector of copper foil with the paste and drying the coating.

The separator for use in the invention can be made from a material which is not limited particularly insofar as the material readily passes the electrolytic solution therethrough, has insulating properties and is chemically stable.

The quaternary ammonium salt of the formula (1) of the invention and the electrolytic solution containing the salt are high in electrical conductivity and solubility in organic solvents, and are suitable for use as an electrolytic solution for electrochemical devices. Examples of electrochemical devices are electric double-layer capacitor, secondary batteries, solar cells of the pigment sensitizer type, electrochromic devices, condenser, etc., which are nevertheless not limitative. Especially suitable as electrochemical devices are electric double-layer capacitor and secondary batteries.

Figure 1:
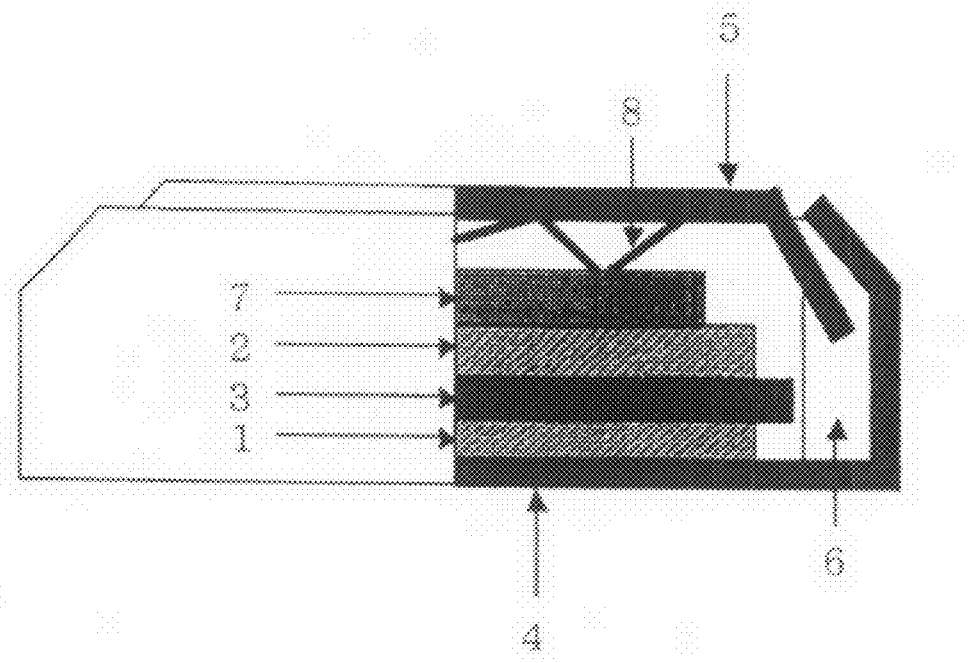
FIG. 1 is a sectional view showing an electric double-layer capacitor of the invention.
Figure 2:
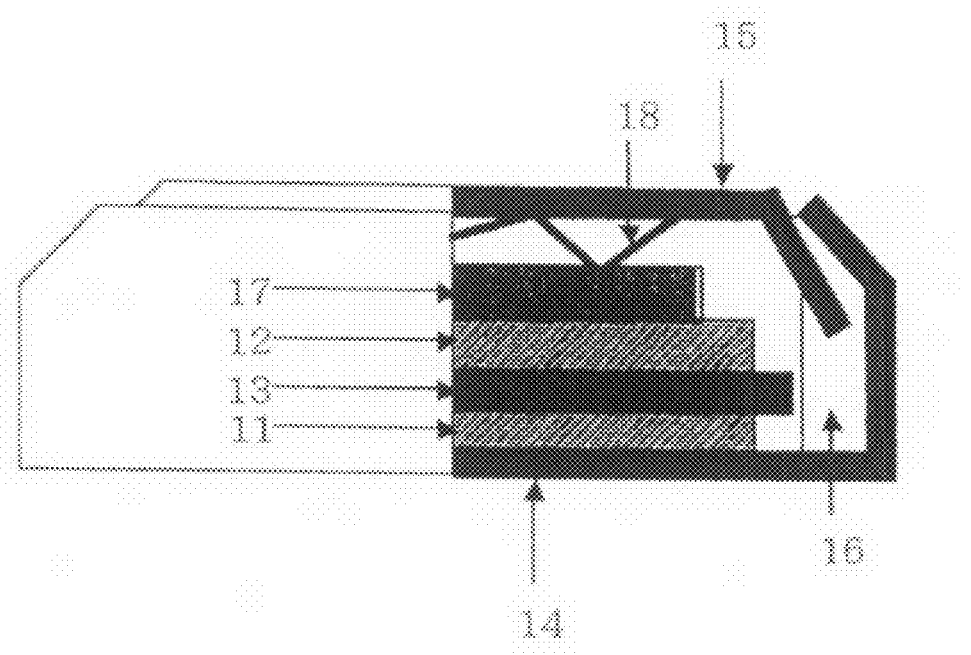
FIG. 2 is a sectional view showing a lithium secondary cell of the invention.

1 electrode, 2 electrode, 3 separator, 4 container member, 5 container member, 6 gasket, 7 spacer, 8 spring, 11 positive electrode, 12 negative electrode, 13 porous separator, 14 positive electrode can, 15 negative electrode can, 16 gasket, 17 spacer, 18 spring

BEST MODE OF CARRYING OUT THE INVENTION

The present invention will be described with reference to the following Examples, but is not limited to these examples. Organic solvents used such as propylene carbonate, acetonitrile, etc. are products of Kishida Chemical Co., Ltd., lithium battery grade. Water content was measured by a Karl Fischer moisture meter (Hiranuma Moisture Meter AQ-7, product of Hiranuma Sangyo Co., Ltd.).

Preparation Example 1

Preparation of
N-methoxymethyl-N-methylpyrrolidinium chloride

A 50.0 g quantity of N-methylpyrrolidine (reagent, product of Tokyo Kasei Co., Ltd., purified by rectification, up to 0.1 wt. % of both of pyrrolidine and water) was dissolved in 292.0 g of dehydrated acetone (up to 0.1 wt. % of water content), followed by replacement with nitrogen. Chloromethyl methyl ether (47.3 g, reagent, product of Tokyo Kasei Co., Ltd., purified by distillation) was added dropwise to the solution at 5° C. over a period of 1 hour. The mixture was stirred at 5 to 15° C. for 4 hours to complete the reaction. The reaction mixture was filtered, and the resulting solid product was washed with 120 g of acetone. The washed product was dried in a vacuum to obtain 92.5 g of the desired product (white solid).

$^1$H-NMR ($CD_3OD$) δ ppm:
2.22 (m 4H), 3.11 (s 3H), 3.46 (m 2H), 3.60 (m 2H), 3.67 (s 3H), 4.65 (s 2H)

Preparation Example 2

Preparation of
N-ethyl-N-methoxymethylpyrrolidinium chloride

A 34.71 g quantity of N-ethylpyrrolidine (reagent, product of Tokyo Kasei Co., Ltd., purified by rectification, up to 0.1 wt. % of both of pyrrolidine and water) was dissolved in 189 g of dehydrated acetone (up to 0.1 wt. % of water content), followed by replacement with nitrogen. Chloromethyl ethyl ether (28.18 g) was added dropwise to the solution at 5° C. over a period of 1 hour. The mixture was stirred at 5° C. for 5 hours to complete the reaction. The reaction mixture was filtered, and the resulting solid product was washed with 100 g of acetone. The washed product was dried in a vacuum to obtain 50.08 g of white solid.

$^1$H-NMR (CD$_3$OD) δ ppm:
1.36 (m 3H), 2.17 (m 4H), 3.41-3.64 (m 6H), 3.64 (s 3H), 4.59 (s 2H)

Preparation Example 3

Preparation of N-ethoxymethyl-N-methylpyrrolidinium chloride

A 87.0 g quantity of N-methylpyrrolidine (reagent, product of Tokyo Kasei Co., Ltd., purified by rectification, up to 0.1 wt. % of both of pyrrolidine and water) was dissolved in 510 g of dehydrated acetone (up to 0.1 wt. % of water content), followed by replacement with nitrogen. Chloromethyl ethyl ether (96.6 g) was added dropwise to the solution at 3° C. over a period of 1 hour. The mixture was stirred at 5 to 15° C. for 4 hours to complete the reaction. The reaction mixture was concentrated and dried in a vacuum at reduced pressure. To the resulting product was added 700 ml of a solvent mixture of 2-butanone/acetone (8/2=v/v) and recrystallized at −30° C. The precipitate was filtered, and the resulting solid product was washed with a solvent mixture of 2-butanone/acetone. The washed product was dried in a vacuum to obtain 183.4 g of the desired product (white crystal).

$^1$H-NMR (CD$_3$OD) δ ppm:
1.30 (t 3H), 2.23 (m 4H), 3.12 (s 3H), 3.47 (m 2H), 3.60 (m 2H), 3.89 (q 2H), 4.71 (s 2H)

Example 1

Preparation of N-methoxymethyl-N-methylpyrrolidinium dicyanamide

In 321.1 g of water was dissolved 68.5 g of N-methoxymethyl-N-methylpyrrolidinium chloride and thereto was added 72.2 g of silver dicyanamide. The mixture was reacted at 50° C. for 9 hours, cooled to room temperature and filtered. The filtrate was concentrated at reduced pressure and dried in vacuum. To the resulting product was added 500 ml of dehydrated dichloromethane (reagent, Kanto Kagaku Co., Ltd.) and cooled to −25° C. The mixture was filtered, concentrated and dried in vacuum. The residue was purified through alumina column (ICN Biomedicals. GmbH, ICN Alumina N, Act.1/eluent acetonitrile). The eluate was concentrated and dried in vacuum to obtain 80.1 g of the desired product (colorless liquid). The product was checked for $^1$H-NMR, electrical conductivity and voltage resistance.

The electrical conductivity was measured using an electrical conductivity meter (product of Radiometer Analytical SAS). The measuring cell used was CDC641T, product of Radiometer Analytical SAS.

The voltage resistance was measured using a 3-electrode electrochemical cell. Used as the working electrode was a glassy carbon electrode (product of BAS Inc.) 1.0 mm in diameter and 0.0079 cm$^{-2}$ in electrode area. The reference electrode used was a silver wire (product of the Nilaco Corp., 99.99% in purity) having a diameter of 0.5 mm. The counter electrode used was a platinum electrode (product of BAS Inc. 11-2233) measuring 0.5 mm in diameter and 50 mm in length. Linear sweep voltammetry was carried out to individually determine the potentials giving an oxidizing current density and reducing current density of 0.5 mAcm$^{-2}$. The difference between the potentials was taken as the voltage resistance. The potential sweep application speed was 50 mVs$^{-1}$. HZ-3000, product of Hokuto Denko Co., Ltd. was used for electrochemical measurement.

$^1$H-NMR (CD$_3$OD) δppm:
2.22 (m 4H), 3.10 (s 3H), 3.45 (m 2H), 3.58 (m 2H), 3.67 (s 3H), 4.60 (s 2H)
electrical conductivity: 21.60 mS/cm (25° C.)
voltage resistance: 4.3V Example 2

Preparation of N-methoxymethyl-N-methylpyrrolidinium thiocyanate

In 260 g of ethanol was dissolved 51.0 g of sodium thiocyanate (reagent, Wako Pure Chemical Ind. Ltd.). In 50.3 g of ethanol was dissolved 80.2 g of N-methoxymethyl-N-methylpyrrolidinium chloride. The latter solution was added dropwise to the former solution at room temperature over a period of 0.5 hour to perform salt exchange. The mixture was stirred at room temperature for 36 hours to complete the reaction and filtered. The resulting solid product was washed with 300 g of ethanol. The filtrate was dried at reduced pressure and the residue was purified through alumina column (ICN Biomedicals. GmbH, ICN Alumina N, Act.1/eluent acetonitrile). The eluate was concentrated and dried in vacuum to obtain 82.0 g of the desired product (colorless liquid). The product was checked for $^1$H-NMR, electrical conductivity and voltage resistance as in Example 1.

$^1$H-NMR(CD$_3$OD) δppm:
2.23 (m 4H), 3.13 (s 3H), 3.49 (m 2H), 3.62 (m 2H), 3.68 (s 3H), 4.65 (s 2H)
electrical conductivity: 14.06 mS/cm (25° C.)
voltage resistance: 3.4V Example 3

Preparation of N-methoxymethyl-N-methylpyrrolidinium nitrate

In 150.4 g of water was dissolved 49.8 g of N-methoxymethyl-N-methylpyrrolidinium chloride and thereto was added 56.1 g of silver nitrate. The mixture was reacted at room temperature for 2 hours, cooled to 5° C. and filtered. The filtrate was concentrated at reduced pressure and dried in vacuum. To the resulting product was added 500 ml of dehydrated dichloromethane (reagent, Kanto Kagaku Co., Ltd.) and cooled to −25° C. The mixture was filtered, concentrated and dried in vacuum. The residue was purified through alumina column (ICN Biomedicals. GmbH, ICN Alumina N, Act.1/eluent acetonitrile). The eluate was concentrated and dried in vacuum to obtain 56.2 g of the desired product (colorless liquid). The product was checked for $^1$H-NMR, electrical conductivity and voltage resistance as in Example 1.

$^1$H-NMR(CD$_3$OD) δppm:
2.20 (m 4H), 3.09 (s 3H), 3.45 (m 2H), 3.58 (m 2H), 3.66 (s 3H), 4.61 (s 2H)
electrical conductivity: 5.96 mS/cm (25° C.)
voltage resistance: 4.2V Example 4

Preparation of N-methoxymethyl-N-methylpyrrolidinium isocyanate

In 325 g of water was dissolved 55.5 g of N-methoxymethyl-N-methylpyrrolidinium chloride and thereto was added 51.0 g of silver cyanate(reagent, Aldrich Corp.). The mixture was reacted at room temperature for 9 hours, cooled to 5° C. and filtered. The filtrate was concentrated at reduced pressure and dried in vacuum. To the resulting product was added 5000 ml of dehydrated ethanol (reagent, Kanto Kagaku Co., Ltd.) and cooled to −25° C. The mixture was filtered, concentrated and dried in vacuum. The residue was purified through alumina column (ICN Biomedicals. GmbH, ICN Alumina N, Act.1/eluent acetonitrile). The eluate was concentrated and dried in vacuum to obtain 43.6 g of the desired product (colorless liquid). The product was checked for $^1$H-NMR, electrical conductivity and voltage resistance as in Example 1.

$^1$H-NMR($CD_3OD$) δppm:

2.21 (m 4H), 3.09 (s 3H), 3.45 (m 2H), 3.58 (m 2H), 3.66 (s 3H), 4.60 (s 2H)

electrical conductivity: 5.81 mS/cm (25° C.)

voltage resistance: 3.3V

Example 5

Preparation of
N-methoxymethyl-N-methylpyrrolidinium nitrite

In 162.3 g of water was dissolved 48.2 g of N-methoxymethyl-N-methylpyrrolidinium chloride and thereto was added 50.7 g of silver nitrite (reagent, Aldrich Corp.). The mixture was reacted at room temperature for 12 hours and at 50° C. for 8 hours, cooled to 5° C. and filtered. The filtrate was concentrated at reduced pressure and dried in vacuum. To the resulting product was added 5000 ml of dehydrated ethanol (reagent, Kanto Kagaku Co., Ltd.) and cooled to −25° C. The mixture was filtered, concentrated and dried in vacuum. The residue was purified through alumina column (ICN Biomedicals. GmbH, ICN Alumina N, Act.1/eluent ethanol). The eluate was concentrated and dried in vacuum to obtain 43.8 g of the desired product (colorless liquid). The product was checked for $^1$H-NMR and electrical conductivity as in Example 1.

$^1$H-NMR($CD_3OD$) δppm:

2.19 (m 4H), 3.08 (s 3H), 3.44 (m 2H), 3.56 (m 2H), 3.65 (s 3H), 4.59 (s 2H)

electrical conductivity: 4.83 mS/cm (25° C.)

Example 6

Preparation of
N-ethyl-N-methoxymethylpyrrolidinium thiocyanate

In 140 g of ethanol was dissolved 27.1 g of sodium thiocyanate (reagent, Wako Pure Chemical Ind. Ltd.). In 20.0 g of ethanol was dissolved 40.0 g of N-ethyl-N-methoxymethylpyrrolidinium chloride. The latter solution was added dropwise to the former solution at room temperature over a period of 0.5 hour to perform salt exchange. The mixture was stirred at room temperature for 36 hours to complete the reaction and filtered. The resulting solid product was washed with 300 g of ethanol. The filtrate was dried at reduced pressure. To the resulting product was added 200 ml of dehydrated chloroform (reagent, Wako Pure Chemical Ind. Ltd.) and cooled to −25° C. The mixture was filtered, concentrated and dried in vacuum. The residue was purified through alumina column (ICN Biomedicals. GmbH, ICN Alumina N, Act.1/eluent acetonitrile). The eluate was concentrated and dried in vacuum to obtain 39.9 g of the desired product (colorless liquid). The product was checked for $^1$H-NMR and electrical conductivity as in Example 1.

$^1$H-NMR ($CDCl_3$) δ ppm:

1.45 (t 3H), 2.33 (m 4H), 3.61 (m 4H), 3.71 (s 3H), 3.80 (m 2H), 4.78 (s 2H)

electrical conductivity: 8.8 mS/cm (25° C.)

Example 7

Preparation of
N-ethoxymethyl-N-methylpyrrolidinium
dicyanamide

In 200.0 g of water was dissolved 42.8 g of N-ethoxymethyl-N-methylpyrrolidinium chloride and thereto was added 44.6 g of silver dicyanamide. The mixture was reacted at 50° C. for 34 hours, cooled to room temperature and filtered. The filtrate was concentrated at reduced pressure and dried in vacuum. To the resulting product was added 500 ml of dehydrated dichloromethane (reagent, Kanto Kagaku Co., Ltd.) and cooled to −25° C. The mixture was filtered, concentrated and dried in vacuum. The residue was purified through alumina column (ICN Biomedicals. GmbH, ICN Alumina N. Act.1/eluent acetonitrile). The eluate was concentrated and dried in vacuum to obtain 45.4 g of the desired product (colorless liquid). The product was checked for $^1$H-NMR and electrical conductivity.

$^1$H-NMR($CDCl_3$) δppm:

1.33 (t 3H), 2.31 (m 4H), 3.20 (s 3H), 3.53 (m 2H), 3.70 (m 2H), 3.91 (q 2H), 4.73 (s 2H)

electrical conductivity: 15.8 mS/cm (25° C.)

Example 8

The N-methoxymethyl-N-methylpyrrolidinium dicyanamide prepared in Example 1 and propylene carbonate were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to 30 ppm in water content. Table 1 shows the concentrations of the solutions. The solutions were checked for electrical conductivity.

<Observation of State of Compositions>

The above compositions were each placed into glass containers having a screw plug inside the dry box, in an amount of 4 cc in each container and brought out of the dry box. The glass containers containing the composition were immersed in a constant-temperature bath and held at 25° C., 0° C. or −30° C. for 5 hours and checked for state visually. The results are shown in Tables, in which "-" indicates separation into two layers, and "solid" represents a solid state.

<Measurement of Electrical Conductivity>

The solution compositions which were found to be in a liquid state free of separation or solidification were brought out of the dry box and checked for electrical conductivity using a conductivity meter (CDM210, product of Radiometer Analytical SAS). The measuring cell used was XE-100 (product of Radiometer Analytical SAS).

TABLE 1

| | electrolyte (wt %) | PC (wt %) | electrical conductivity | | |
|---|---|---|---|---|---|
| | | | (25° C.) (mS/cm) | (0° C.) (mS/cm) | (−30° C.) (mS/cm) |
| Ex. 8 | 20 | 80 | 17.2 | 10.8 | 4.5 |
| | 30 | 70 | 20.4 | 12.7 | 4.9 |
| | 40 | 60 | 22.6 | 13.4 | 4.9 |
| | 60 | 40 | 23.4 | 13.2 | 4.5 |
| | 80 | 20 | 22.8 | 12.3 | 4.2 |
| | 100 | 0 | 21.6 | 10.2 | 2.7 |

Example 9

The solutions were checked for electrical conductivity in the same manner as in Example 8 with the exception of using N-methoxymethyl-N-methylpyrrolidinium dicyanamide prepared in Example 1 and acetonitrile.

TABLE 2

| | electrolyte (wt %) | AN (wt %) | electrical conductivity | | |
|---|---|---|---|---|---|
| | | | (25° C.) (mS/cm) | (0° C.) (mS/cm) | (−30° C.) (mS/cm) |
| Ex. 9 | 20 | 80 | 50.4 | 44.3 | 29.6 |
| | 40 | 60 | 68.8 | 51.4 | 32.9 |
| | 50 | 50 | 70.0 | 53.5 | 32.1 |
| | 60 | 40 | 67.2 | 49.4 | 27.4 |
| | 80 | 20 | 48.1 | 30.3 | 14.1 |
| | 100 | 0 | 21.6 | 10.2 | 2.7 |

Example 10

The solutions were checked for electrical conductivity in the same manner as in Example 8 with the exception of using N-methoxymethyl-N-methylpyrrolidinium thiocyanate prepared in Example 2 and propylene carbonate.

TABLE 3

| | electrolyte (wt %) | PC (wt %) | electrical conductivity | | |
|---|---|---|---|---|---|
| | | | (25° C.) (mS/cm) | (0° C.) (mS/cm) | (−30° C.) (mS/cm) |
| Ex. 10 | 20 | 80 | 15.3 | 9.4 | 3.4 |
| | 40 | 60 | 19.3 | 10.7 | 3.3 |
| | 60 | 40 | 19.1 | 9.9 | 2.9 |
| | 80 | 20 | 17.0 | 8.1 | 2.1 |
| | 100 | 0 | 14.1 | 6.4 | 1.5 |

Example 11

The solutions were checked for electrical conductivity in the same manner as in Example 8 with the exception of using N-methoxymethyl-N-methylpyrrolidinium thiocyanate prepared in Example 2 and acetonitrile.

TABLE 4

| | electrolyte (wt %) | AN (wt %) | electrical conductivity | | |
|---|---|---|---|---|---|
| | | | (25° C.) (mS/cm) | (0° C.) (mS/cm) | (−30° C.) (mS/cm) |
| Ex. 11 | 20 | 80 | 43.4 | 35.4 | 23.6 |
| | 40 | 60 | 60.0 | 45.4 | 27.9 |
| | 50 | 50 | 60.9 | 44.8 | 25.4 |
| | 60 | 40 | 58.2 | 40.1 | 21.5 |
| | 80 | 20 | 40.5 | 23.7 | 8.7 |
| | 100 | 0 | 14.1 | 6.4 | 1.5 |

Example 12

The solutions were checked for electrical conductivity in the same manner as in Example 8 with the exception of using N-methoxymethyl-N-methylpyrrolidinium nitrate prepared in Example 3 and propylene carbonate.

TABLE 5

| | electrolyte (wt %) | PC (wt %) | electrical conductivity (25° C.) (mS/cm) |
|---|---|---|---|
| Ex. 12 | 20 | 80 | 12.0 |
| | 40 | 60 | 13.7 |
| | 60 | 40 | 12.1 |
| | 80 | 20 | 9.1 |
| | 100 | 0 | 6.0 |

Example 13

The solutions were checked for electrical conductivity in the same manner as in Example 8 with the exception of using N-methoxymethyl-N-methylpyrrolidinium nitrate prepared in Example 3 and acetonitrile.

TABLE 6

| | electrolyte (wt %) | AN (wt %) | electrical conductivity (25° C.) (mS/cm) |
|---|---|---|---|
| Ex. 13 | 20 | 80 | 35.7 |
| | 40 | 60 | 46.6 |
| | 60 | 40 | 44.5 |
| | 80 | 20 | 27.9 |
| | 100 | 0 | 6.0 |

Example 14

The solutions were checked for electrical conductivity in the same manner as in Example 8 with the exception of using N-ethyl-N-methoxymethylpyrrolidinium thiocyanate prepared in Example 6 and acetonitrile.

TABLE 7

| | electrolyte (wt %) | AN (wt %) | electrical conductivity | |
|---|---|---|---|---|
| | | | (25° C.) (mS/cm) | (−30° C.) (mS/cm) |
| Ex. 14 | 20 | 80 | 39.6 | 19.4 |
| | 40 | 60 | 52.3 | 20.9 |
| | 60 | 40 | 50.5 | 15.3 |
| | 80 | 20 | 32.4 | 5.3 |
| | 100 | 0 | 8.8 | solid |

Example 15

The solutions were checked for electrical conductivity in the same manner as in Example 8 with the exception of using N-ethoxymethyl-N-methylpyrrolidinium dicyanamide prepared in Example 7 and acetonitrile.

TABLE 8

|  | electrolyte (wt %) | AN (wt %) | electrical conductivity (25° C.) (mS/cm) | (−30° C.) (mS/cm) |
|---|---|---|---|---|
| Ex. 15 | 20 | 80 | 45.3 | 22.0 |
|  | 40 | 60 | 59.1 | 23.7 |
|  | 60 | 40 | 55.6 | 17.4 |
|  | 80 | 20 | 39.2 | 8.5 |
|  | 100 | 0 | 15.8 | 1.5 |

Comparative Example 1

Preparation of N-methoxyethyl-N-methylpyrrolidinium tetrafluoroborate

N-methylpyrrolidine (31.10 g, reagent, product of Tokyo Kasei Co., Ltd.) was dissolved in 124.30 g of toluene, followed by replacement with nitrogen. To the solution was added dropwise 61.22 g of bromoethyl methyl ether (reagent, product of Aldrich Corp.) at 27° C. over a period of 1 hour. The mixture was heated to a gradually raised temperature and then stirred at 60 to 70° C. for 37 hours to terminate the reaction. The reaction mixture was cooled to room temperature, and the resulting solids were filtered off under a nitrogen stream. The filter cake was washed with 70 g of toluene and thereafter dried in a vacuum (giving 78.99 g of a brown solid product). The solid product obtained was suspended in 200 g of acetone, and the suspension was stirred at room temperature, followed by washing with stirring at room temperature and filtration under a nitrogen stream. (This procedure was repeated twice.) The product was dried in a vacuum to result in a yield of 62.64 g. The product, which was colored, was dissolved in 131.83 g of water, 6.00 g of activated carbon (Carboraffin, product of Takeda Pharmaceutical Co., Ltd.) was added to the solution, and the mixture was stirred at 90 to 95° C. for 12 hours. The mixture was cooled to room temperature, and the activated carbon was separated off by filtration. The filtrate was concentrated in a vacuum, followed by drying in a vacuum to result in a yield of 58.34 g. The product was dissolved in a solvent mixture of 200.48 g of acetone and 27.22 g of chloroform with heating for recrystallization. The resulting white solids obtained were filtered off in a nitrogen stream, washed with 50 g of acetone and dried in a vacuum, giving 34.10 g of N-methoxyethyl-N-methylpyrrolidinium bromide.

$^1$H-NMR (CD$_3$OD) δ ppm: 2.24 (m 4H), 3.15 (s 3H), 3.40 (s 3H), 3.65 (m 6H), 3.83 (m 2H)

Subsequently, 40.0 g of the N-methoxyethyl-N-methylpyrrolidinium bromide prepared was dissolved in 40.0 g of MeOH, and 54.0 g of methanol solution of 30 wt. % HBF$_4$ was added to the solution. The mixture was heated at 130° C. in a nitrogen stream to remove hydrogen chloride produced as a by-product and an excess of HBF$_4$, giving 39.9 g of the desired product (white solid).

$^1$H-NMR (CD$_3$OD) δ ppm: 2.22 (m 4H), 3.10 (S 3H), 3.39 (S 3H), 3.58 (m 6H), 3.81 (m 2H)

The solutions were checked for electrical conductivity in the same manner as in Example 8 with the exception of using the above N-methoxyethyl-N-methylpyrrolidinium tetrafluoroborate and propylene carbonate.

TABLE 9

|  | electrolyte (wt %) | PC (wt %) | electrical conductivity (25° C.) (mS/cm) |
|---|---|---|---|
| Com. Ex. 1 | 20 | 80 | 12.2 |
|  | 40 | 60 | 13.0 |
|  | 60 | 40 | 10.1 |
|  | 80 | 20 | 6.3 |
|  | 100 | 0 | 2.8 |

INDUSTRIAL APPLICABILITY

A quaternary ammonium salt of the formula (1), and an electrolytic solution containing the salt of the present invention are highly soluble in organic solvents, highly reliable at low temperatures and highly electrically conductive, and are suitable for an electrolyte for electrochemical devices. Further, these quaternary ammonium salts are free of halogen and an electrolytic solution can be obtained which is less likely to burden the environment.

The invention claimed is:

1. A quaternary ammonium salt of the formula (1)

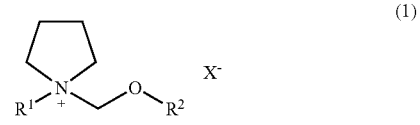

(1)

wherein R$^1$ is straight-chain or branched alkyl having 1 to 4 carbon atoms, R$^2$ is straight-chain or branched alkyl having 1 to 3 carbon atoms, and X$^-$ is N(CN)$_2^-$ or SCN$^-$.

2. A quaternary ammonium salt of the formula (2)

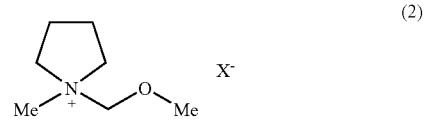

(2)

wherein X$^-$ is N(CN)$_2^-$ or SCN$^-$, and Me is methyl.

3. A composition wherein the composition comprises at least the quaternary ammonium salt of claim 1 and an organic solvent.

4. A composition according to claim 3 wherein the organic solvent is at least one selected from among cyclic carbonic acid esters, chain carbonic acid esters, phosphoric acid esters, cyclic ethers, chain ethers, lactone compounds, chain esters, nitrile compounds, amide compounds and sulfone compounds.

5. A composition according to claim 4 wherein the organic solvent is at least one selected from among ethylene carbonate, propylene carbonate, dimethyl carbonate, ethylmethyl carbonate, dimethoxyethane and acetonitrile.

6. A composition according to claim 4 wherein the organic solvent is at least one selected from among propylene carbonate and acetonitrile.

7. An electrochemical device which includes an electrolytic solution comprising an electrolyte of the formula (3)

wherein $R^1$ is straight-chain or branched alkyl having 1 to 4 carbon atoms, $R^2$ is straight-chain or branched alkyl having 1 to 3 carbon atoms, and $X^-$ is $N(CN)_2^-$ or $SCN^-$, and an organic solvent, the organic solvent being at least one selected from propylene carbonate and acetonitrile.

8. A process for preparing a quaternary ammonium salt of the formula (1)

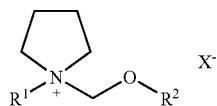
(1)

wherein $R^1$ is straight-chain or branched alkyl having 1 to 4 carbon atoms, $R^2$ is straight-chain or branched alkyl having 1 to 3 carbon atoms, and $X^-$ is $N(CN)_2^-$ or $SCN^-$, comprising (a) a step of reacting an alkylpyrrolidine of the formula (5) and a compound of the formula (6) to prepare a quaternary ammonium salt of the formula (1a)

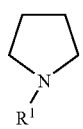
(5)

wherein $R^1$ is straight-chain or branched alkyl having 1 to 4 carbon atoms,

(6)

wherein $R^2$ is straight-chain or branched alkyl having 1 to 3 carbon atoms and Y Cl, Br or I,

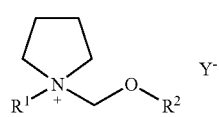
(1a)

wherein $R^1$, $R^2$ and Y are same as defined above, and (b) a step of reacting the quaternary ammonium salt of the formula (1a) and a compound of the formula (7)

MX (7)

wherein M is hydrogen, alkali metal atom, alkaline earth metal atom or metal atom, and $X^-$ is $N(CN)_2^-$ or $SCN^-$.

* * * * *